United States Patent [19]

Kawahara et al.

[11] 4,109,079

[45] Aug. 22, 1978

[54] STABILIZED S-ADENOSYL-L-METHIONINE PREPARATIONS

[75] Inventors: Toshihisa Kawahara; Goro Motoki; Kazuo Uchida; Hiroshi Yoshino, all of Choshi, Japan

[73] Assignee: Yamasa Shoyu Kabushiki Kaisha, Japan

[21] Appl. No.: 732,287

[22] Filed: Oct. 14, 1976

[30] Foreign Application Priority Data

Oct. 16, 1975 [JP] Japan .................. 50-123775
Apr. 9, 1976 [JP] Japan .................. 57-39313

[51] Int. Cl.² .......................... C07H 19/16
[52] U.S. Cl. .................. 536/26; 424/180; 536/22
[58] Field of Search .................. 536/26, 22

[56] References Cited

U.S. PATENT DOCUMENTS

| | | | |
|---|---|---|---|
| 2,946,781 | 7/1960 | Shunk et al. | 536/26 |
| 2,969,353 | 1/1961 | Shunk et al. | 536/26 |
| 3,707,536 | 12/1972 | Haid et al. | 536/26 |
| 3,893,999 | 7/1975 | Fiecchi | 536/26 |
| 3,954,726 | 5/1976 | Fiecchi | 536/26 |

*Primary Examiner*—Johnnie R. Brown
*Attorney, Agent, or Firm*—Wenderoth, Lind & Ponack

[57] ABSTRACT

A stabilized dry S-adenosyl-L-methionine preparation is obtained by incorporating about 1 - 10 parts by weight of lithium in the form of a salt with 100 parts by weight of S-adenosyl-L-methionine or a low-toxicity salt thereof. According to the invention, instability of S-adenosyl-L-methionine or a salt thereof is substantially eliminated. The stabilized dry preparation is very useful as medical drugs and reagents for biochemical research.

12 Claims, No Drawings

STABILIZED S-ADENOSYL-L-METHIONINE PREPARATIONS

BACKGROUND OF THE INVENTION

1. Field of the Invention

This invention relates to a stabilized dry preparation of S-adenosyl-L-methionine or a low-toxicity salt thereof and a process for production of the preparations.

2. Description of the Prior Art

S-adenosyl-L-methionine (hereinafter referred to as SAM) exists in numerous kinds of organisms such as animals, plants and microorganisms in the natural world, and is a psysiologically active substance which plays an important role as a methyl group donor of methylation reaction by way of various transmethylases in living organisms. For example, SAM is an indispensable substance which serves as the methyl group donor in the transmethylation reaction such as methylation of high molecular substances in vivo of nucleic acid, protein, fat and the like which are essential for maintaining life, formation of creatine from guanidinoacetate and formation of choline from aminoethanol. Consequently, SAM is expected to be useful as a chemotherapeutant, and the therapeutic values for hepatopias, hyperdislipidemias, generalized or local arteriosclerosis, psychiatric manifestations of depressive and neurological type, degenerative arthromathies, neurological algic manifestation, disturbance of the sleeping-waking rhythm, etc., have been reported. Thus, the use of SAM in medical drugs will be developed if instability of SAM is eliminated.

From the viewpoint of practical use of SAM in medical drugs, however, SAM is very unstable even at room temperature. Therefore, it has been a serious problem that SAM alone can hardly be used as reagents for biochemical research and medical drugs. Hitherto have been known SAM salts such as the iodide, bromide, Reinecke's salt, hydrochloride and sulfate thereof, but all of these salts are unstable. For example, stability of dry SAM hydrochloride at 37° C is shown in Table 1.

Table 1

| Storage time (day) | 0 | 2 | 4 | 10 | 30 | 60 |
|---|---|---|---|---|---|---|
| SAM undecomposed (%) | 100 | 66.9 | 53.1 | 35.1 | 20.2 | 12.5 |

The "SAM undecomposed (%)" was obtained in the following way:
 a. the sample is sealed into ampoules 3 ml. in capacity,
 b. they are stored at a predetermined temperature for given days,
 c. then they are dissolved in distilled water,
 d. a determined amount of the solution is subjected to paper electrophoresis by employing 3% acetic acid solution,
 e. it is then subjected to paper chromatography in the direction at a right angle with the direction of electrophoretic migration using the developer of ethanol:acetic acid:water (65:1:34),
 f. spots of SAM and those of other decomposed substances are detected by means of an ultraviolet-ray detector,
 g. these spots are extracted with 0.1 N hydrochloric acid,
 h. absorbances at 260 nm of the extracts are measured, and
 i. ratio of absorbance is calculated according to the following formula, which represents the residual ratio of SAM. The term "O.D. 260" stands for optical density at 260 nm.

$$SAM \text{ undecomposed } (\%) = \frac{O.D.\ 260 \text{ of } SAM}{\text{The Whole } O.D.\ 260} \times 100$$

SAM p-toluenesulfonate and a double salt of SAM p-toluenesulfonate and sulfate are known as stable SAM salts (Japanese laid-open patent publication Nos. 92215/1974 and 76215/1975). SAM p-toluenesulfonate, however, has a defect in that complicated purification treatment is required in the course of production thereof.

Much research has been conducted to produce an SAM preparation having excellent stability in comparison with conventional dry SAM salts. The present inventors have found that a novel preparation comprising an SAM salt and a lithium salt has a markedly improved effect on the stability of SAM.

SUMMARY OF THE INVENTION

An object of the invention is to provide a novel and stabilized dry SAM preparation which is useful in medical drugs or reagents for biochemical research.

Other and further objects, features and advantages of the invention will appear more fully from the following description.

In other words, in accordance with the present invention, a stabilized SAM preparation is provided by a simpler method and is expected to contribute largely to biochemical research on SAM and medical applications of SAM. Incidentally, SAM has been expected to have very useful applications but its development has been blocked owing to its marked instability.

The stabilized dry preparations of S-adenosyl-L-methionine of the present invention comprises S-adenosyl-L-methionine or a low-toxicity salt thereof and a lithium salt added thereto in an effective amount and preferably in an amount of about 1 to 10% by weight on the conversion basis of lithium based on the amount of S-adenosyl-L-methionine.

DETAILED DESCRIPTION OF THE INVENTION

Processes for producing SAM itself or the salts thereof do not constitute any part of the present invention. For example, SAM is produced by; (i) a process in which yeast of Saccharomyces, Candida, Torulopsis or the like, or mold of Asperlgillus, Penicillium, Mucor, Rhizopus or the like, is cultured in a methionine-containing medium to accumulate SAM in the fungus, followed by extracting the resulting SAM with an extracting agent such as trichloroacetic acid, perchloric acid and an acetic ester; or (ii) an enzymatic process in which SAM is synthesized from adenosine triphosphate and methionine in the presence of methionineadenosyltransferase transferase. An SAM-containing liquid thus obtained is fractionated by column chromatography using a weakly acidic cation exchange resin, a strongly acidic cation exchange resin or a chelate resin to obtain an eluent. A SAM salt can be purified and isolated by subjecting the eluent to precipitation with a hydrophilic organic solvent or a hydrophilic organic solvent solution of phosphotungstic acid, picric acid, picrolonic acid or the like.

The type of SAM salt to be employed in the present invention is not restricted to any particular one as long as its toxicity is low and it can be used as reagents for biochemical researches and/or medical drugs. All the lowtoxicity SAM salts can be used in the present invention, and are typically exemplified by hydrochloride, sulfate, iodide, bromide and Reinecke's salt thereof.

The lithium salts which, together with SAM or a salt thereof, produce the stabilized dry SAM preparation are not restricted to particular ones as long as the lithium salts dissociate and dissolve in an acidic solution, do not make the solution alkaline, and preferably are of pharmacologically low toxicity. Such lithium salts, for example, include a lithium halide such as lithium chloride, lithium iodide and lithium bromide, an inorganic acid salt of lithium such as lithium sulfate, lithium nitrate, lithium phosphate, lithium borate, and lithium carbonate, and an aliphatic or aromatic mono- or polycarboxylic acid salt of lithium, of which the number of carbon atom other than that of carboxylic group being preferably 0 to about 9 preferably a mono or dicarboxylate, such as lithium formate, lithium acetate, lithium citrate, lithium succinate and lithium benzoate. Among these, lithium halides and lithium salts of a strong inorganic acid such as sulfate are preferable.

When producing a SAM salt preparation in which a lithium salt coexists, it is desirable to disperse the lithium salt into the SAM as homogeneously as possible. Usually, SAM or a SAM salt and a lithium salt are dissolved in the same solution and then subjected to drying to obtain the dry preparation. In other words, a SAM salt and a lithium salt are homogeneously dispersed in the same solution by either dissolving the lithium salt in an acidic SAM solution, dissolving the SAM salt in an acidic lithium salt solution, or dissolving them simultaneously in an acidic solution, whereby a dry preparation is produced upon drying of the solution. The object of the present invention is fundamentally performed by the presence of a lithium salt (or lithium ion) in the dry SAM preparation. Therefore, any other methods for production which perform the object can be advantageously employed.

As the solvent for SAM salts and lithium salts can be empoloyed those having a large solubility for the SAM salt and lithium salt and which are not reactive with them. Water or a mixture of water and a hydrophilic organic solvent such as an alcohol, e.g., methanol, or ethanol, a ketone, e.g., acetone and an ether, e.g., dioxane can be employed as the solvent therefor. It is necessary to adjust pH of the solution to not more than 7 and preferably not more than 3 since SAM is rapidly decomposed under alkaline conditions.

For producing a dry preparation from an SAM salt and a lithium salt, it is desirable to employ a process which can dry the mixture thereof at a lower temperature and in a shorter period of time from the viewpoint of instability of the SAM salt in a solution state and at a high temperature. Such drying method may be exemplified by a freeze-drying method. The dry preparation can also be produced by adding to a dry mixture of or a solution of a mixture of a SAM salt and a lithium salt one or two or more kinds of hydrophilic organic solvents which are selected depending on the type of the salts and the type of the solvent used for the solution of SAM and the lithium salt, followed by subjecting the resulting mixture to precipitation and drying. These processes may be carried out in a suitable combination with a reduced or vacuum drying method in the presence or the absence of a desiccating agent such as phosphorus pentoxide, calcium chloride, silica gel and concentrated sulfuric acid. In any process, it is desirable to employ a drying temperature of not higher than 35° C and preferably not higher than 25° C. Degree of drying of the SAM preparation is generally not more than 3% and preferably not more than 1% by weight of moisture in the preparation. The stabilized dry SAM preparation is obtained by storing it in an air-tight vessel to prevent moisture absorption after the drying.

In order to appreciate the excellent results obtained by the present invention, an SAM preparation was produced by dissolving SAM hydrochloride in water (pH 2), adding thereto 2 mole equivalents (based on the SAM hydrochloride) of lithium chloride, and then subjecting the mixture to freeze-drying. The stabilities of the SAM preparation at 37° C are shown in Table 2, in contrast to those of SAM hydrochloride in the absence of lithium chloride. The data in the table show the SAM undecomposed (%).

Table 2

| Samples | Storage time (day) | | | | |
|---|---|---|---|---|---|
| | 0 | 3 | 10 | 30 | 60 |
| Dry preparation of the invention | 100 | 100 | 100 | 99.0 | 99.2 |
| Control sample | 100 | 58.2 | 34.6 | 21.0 | 11.6 |

Moreover, the effects of various lithium salts on the stability of SAM hydrochloride are shown in Table 3. The stability test was carried out at 37° C and for 3 days of storage.

Table 3

| Kind of lithium salt | Amount of lithium salt / Amount of SAM salt (%) | | | | | | | |
|---|---|---|---|---|---|---|---|---|
| | 0 | 2 | 4 | 6 | 10 | 20 | 30 | 50 |
| Lithium chloride | 60.9 | 69.9 (0.3%) | 78.5 (0.6%) | 90.2 (1.0%) | 97.8 (1.6%) | 100 (3.2%) | 100 (4.8%) | 100 (8.0%) |
| Lithium sulfate | 60.9 | 64.5 (0.1%) | 74.2 (0.2%) | 79.1 (0.4%) | 86.5 (0.6%) | 93.1 (1.2%) | 98.2 (1.9%) | 100 (3.2%) |
| Lithium bromide | 60.9 | 68.8 (0.2%) | 77.6 (0.3%) | 84.0 (0.5%) | 92.2 (0.8%) | 98.8 (1.6%) | 100 (2.4%) | 100 (4.0%) |

In Table 3, the ratio of SAM salt to lithium salt is represented by weight percent, and weight of the SAM salt was determined by calculating the concentration thereof from O.D. (optical density) of the solution on the assumption that $\epsilon = 15,400$. The numerals in parentheses stand for percentages converted to lithium basis. As clearly shown in Tables 2 and 3, a conventional dry SAM salt preparation containing no lithium salt is unstable, whereas the SAM salt preparations containing various lithium salts according to the present invention are very stable.

As shown in Table 3, the effective amounts of lithium salts to be added vary depending on the kind of lithium salt. The amount of addition, therefore, is to be determined depending on the kind of lithium salt. For example, lithium chloride is preferably to be not less than 20% by weight, lithium sulfate is preferably not less than 50% by weight, and lithium bromide is preferably not less than 30% by weight on the basis of SAM.

As described above, the amount of lithium salts to be comprised in the SAM salt preparations of the present invention cannot be determined precisely as a whole owing to difference in the kind of SAM salts and the degree of dissociation of lithium salts in acidic solutions and the like. Satisfactory results, however, are obtained by allowing a lithium salt to be present in the SAM preparation of the present invention, in an amount as a lithium metal of about 1 to 10% by weight and preferably about 3 to 7% by weight of SAM.

The present invention will be understood more readily by reference to the following examples; however, these examples are intended to illustrate the invention and are not to be construed to limit the scope of the invention.

EXAMPLE 1

SAM was extracted from 320 g of bread yeast which had been grown in Schlenk's medium whereby SAM had been accumulated therein, with 2.0 l. of 1.5 N perchloric acid, and the extract was adsorbed on a column of the chelate resin "DIAION CR-10" (trade name, supplied by Mitsubishi Chemical Industries, Japan) (H-type), followed by elution of the SAM content with hydrochloric acid. After concentrating the eluate, methanol-acetone was added thereto to obtain 2.0 g of SAM hydrochloride.

The SAM hydrochloride was then subjected to a process which comprised dissolving it in distilled water, adjusting pH of the resulting solution to 3.0 with the strongly basic anion exchange resin "DOWEX 2X-8" (carbonic acid-type) (trade name, supplied by Dow Chemical), adding thereto 400 mg of lithium chloride, pipetting 0.5 ml. each of the resulting solution into ampoules 3 ml. in capacity, subjecting them to freeze-drying, further drying them under reduced pressure for 2 hours in the presence of phosphorus pentoxide and then sealing the ampoules, to obtain a dry SAM salt preparation (moisture 0.9%).

The results of storage test of the preparation at 37° C are shown in the following table.

| Storage time (day) | 10 | 20 | 30 | 60 |
|---|---|---|---|---|
| SAM undecomposed (%) | 100 | 100 | 99.0 | 99.2 |

EXAMPLE 2

The process of Example 1 was repeated except for the use of sulfuric acid instead of hydrochloric acid for eluting SAM content from the chelate resin, to obtain a dry SAM sulfate-lithium chloride preparation.

The results of storage test of this preparation are shown in the following table.

| Storage time (day) | 10 | 20 | 30 | 60 |
|---|---|---|---|---|
| SAM undecomposed (%) | 100 | 100 | 100 | 99.1 |

EXAMPLE 3

About 2.0 l. of the extract of SAM obtained in the same way as in Example 1 with 1.5 N perchloric acid was adsorbed on a column of the weakly acidic cation exchange resin "AMBERITE IRC-50" (trade name, supplied by Rohm & Haas) (H-type) and then eluted with sulfuric acid. The eluate was then subjected to a process which comprised adjusting the pH thereof to 5.6, subjecting SAM content to precipitation with phosphorus tungstate, extracting it with acetone, adding thereto 1M tetraethylammonium bromide, concentrating the mixture, and then allowing it to precipitate with methanol, to obtain 2.5 g of SAM bromide.

The SAM bromide was further subjected to a process which comprised dissolving it in distilled water, adjusting the pH of the solution to 5.0 in the same way as in Example 1, adding thereto 500 mg of lithium bromide, drying the mixture in the same way as in Example 1, and sealing ampoules, to obtain dry SAM bromide preparation.

The results of storage test of this preparation at 37° C, "SAM undecomposed (%)," are shown in the following table. As a control, was employed a dry preparation produced in the same way without addition of lithium bromide.

| Samples | Storage time (day) | | | |
|---|---|---|---|---|
| | 10 | 20 | 30 | 60 |
| Dry preparation | 100 | 98.2 | 97.6 | 97.7 |
| Control preparation | 40.2 | 19.6 | 12.2 | 7.6 |

What we claim is:

1. A stabilized dry S-adenosyl-L-methionine preparation which comprises S-adenosyl-L-methionine or a pharmaceutically acceptable salt thereof and an effective amount of a lithium salt which is pharmaceutically acceptable and is soluble in an acidic solution of the S-adenosyl-L-methionine or a pharmaceutically acceptable salt thereof and does not make the solution alkaline.

2. The preparation as set forth in claim 1, in which the preparation contains not more than 3% by weight of moisture.

3. The preparation as set forth in claim 1, in which the S-adenosyl-L-methionine salt is selected from the group consisting of the hydrochloride, sulfate, iodide, bromide and Reinecke's salt thereof.

4. The preparation as set forth in claim 1, in which the lithium salt is selected from the group consisting of lithium chloride, lithium bromide, lithium iodide, lithium sulfate, lithium nitrate, lithium phosphate, lithium borate, lithium carbonate, lithium formate, lithium acetate, lighium citrate, lithium succinate and lithium benzoate.

5. The preparation as set forth in claim 1, in which the preparation comprises S-adenosyl-L-methionine or a pharmaceutically acceptable salt thereof and a lithium salt which is pharmaceutically acceptable and is soluble in an acidic solution of the S-adenosyl-L-methionine or a pharmaceutically acceptable salt thereof and does not make the solution alkaline, added thereto in an amount of about 1 to 10% by weight as lithium of the amount of S-adenosyl-L-methionine.

6. The preparation as set forth in claim 5, in which the preparation contains not more than 2% by weight of moisture.

7. The preparation as set forth in claim 5, in which the S-adenosyl-L-methionine salt is selected from the group consisting of the hydrochloride, sulfate, iodide, bromide and Reinecke's salt thereof.

8. The preparation as set forth in claim 5, in which the lithium salt is selected from the group consisting of lithium chloride, lithium bromide, lithium iodide, lithium sulfate, lithium nitrate, lithium borate, lithium carbonate, lithium formate, lithium acetate, lithium citrate, lithium succinate and lithium benzoate.

9. The preparation as set forth in claim 5, in which the S-adenosyl-L-methionine salt is hydrochloride thereof.

10. The preparation as set forth in claim 9, in which the lithium salt is a halide thereof.

11. The preparation according to claim 1 wherein the lithium salt is selected from the group consisting of chloride, bromide, sulfate, carbonate, acetate, citrate and succinate.

12. The preparation according to claim 5 wherein the lithium salt is selected from the group consisting of chloride, bromide, sulfate, carbonate, acetate, citrate and succinate.

* * * * *